(12) United States Patent
Serafini et al.

(10) Patent No.: US 9,428,442 B2
(45) Date of Patent: Aug. 30, 2016

(54) PROCESS FOR THE PREPARATION OF CLOMIPHENE

(71) Applicant: F.I.S.—FABBRICA ITALIANA SINTETICI S.P.A., Montecchio Maggiore (VI) (IT)

(72) Inventors: Siro Serafini, Vicenza (IT); Pierluigi Padovan, Montecchio Maggiore (IT)

(73) Assignee: F.I.S.—FABBRICA ITALIANA SINTETICI S.P.A., Montecchio Maggiore (VI) (IT)

( * ) Notice: Subject to any disclaimer, the term of this patent is extended or adjusted under 35 U.S.C. 154(b) by 0 days.

(21) Appl. No.: 14/869,065

(22) Filed: Sep. 29, 2015

(65) Prior Publication Data

US 2016/0152551 A1 Jun. 2, 2016

(30) Foreign Application Priority Data

Oct. 28, 2014 (EP) .................................... 14190736

(51) Int. Cl.
*C07C 213/08* (2006.01)
*C07F 9/6574* (2006.01)

(52) U.S. Cl.
CPC ......... *C07C 213/08* (2013.01); *C07F 9/65744* (2013.01); *C07B 2200/09* (2013.01)

(58) Field of Classification Search
CPC .................... C07C 213/08; C07B 2200/09
See application file for complete search history.

(56) References Cited

U.S. PATENT DOCUMENTS

| 2,914,563 A | 11/1959 | Allen et al. |
| 5,118,832 A | 6/1992 | Pearson |
| 6,632,841 B1 * | 10/2003 | Af Ursin ................ A61K 47/20 514/422 |

FOREIGN PATENT DOCUMENTS

CN 103351304 10/2013

OTHER PUBLICATIONS

Szumigala, Ronald H., et al., "Facile Synthesis of 2-Bromo-3-Fluorobenzonitrile: An Application . . . ", The Journal of Organic Chemistry, vol. 69, No. 2, pp. 566-569, 2004.
Search Report issued in corresponding European Patent Application No. EP14190736, filed Oct. 14, 2015.

* cited by examiner

*Primary Examiner* — Golam M M Shameem
(74) *Attorney, Agent, or Firm* — Lucas & Mercanti, LLP

(57) ABSTRACT

An improved process for the preparation of the active pharmaceutical ingredient Clomiphene and, in particular, trans-Clomiphene, using acetic acid or trifluoroacetic acid is disclosed.

12 Claims, 5 Drawing Sheets

PROCESS FOR THE PREPARATION OF CLOMIPHENE

CROSS-REFERENCE TO RELATED APPLICATIONS

This application claims the benefit of priority from European Patent Application No. EP 14190736.0, filed Oct. 28, 2014, the disclosure of which is incorporated herein.

TECHNICAL FIELD

The present invention refers to a process for the preparation the active pharmaceutical ingredient named Clomiphene and, in particular, trans-Clomiphene.

BACKGROUND ART

Clomiphene is an active pharmaceutical ingredient used as ovulatory stimulant to treat ovulatory dysfunction and polycystic ovary syndrome.

Clomiphene has chemical name Ethanamine, 2-[4-(2-chloro-1,2-diphenylethenyl)phenoxy]-N,N-diethyl and it is a mixture of the geometric isomers trans-Clomiphene of chemical formula (I) and cis-Clomiphene of chemical formula (II):

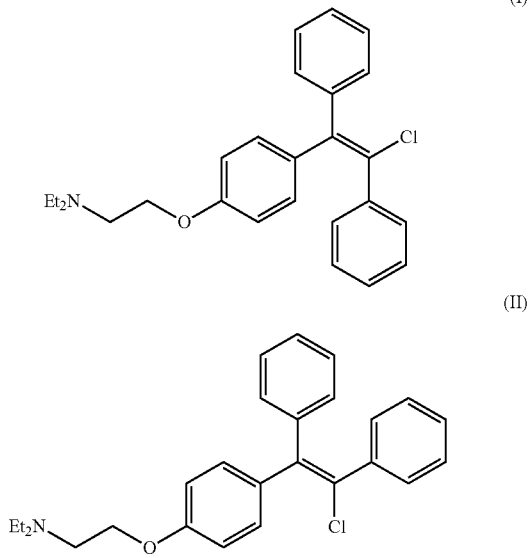

The pharmaceutical products currently on the market containing Clomiphene, typically as monocitrate salt, comprise Clomiphene having the following composition: from 50% to 70% of trans-clomiphene and from 30% to 50% of cis-Clomiphene.

Trans-Clomiphene of chemical formula (I), also named Enclomiphene or E-Clomiphene, as monocitrate salt, is currently under evaluation in clinical phase III for the treatment of secondary hypergonadism. Moreover, it is also said that trans-Clomiphene could be potentially used for an adjuvant therapy in hypogonadal men with Type 2 diabetes.

U.S. Pat. No. 3,848,030, in examples 31 and 32, discloses a process for the resolution of the geometric isomers of Clomiphene through the preparation of salts with racemic binaphthyl-phosphoric acid.

In the later publication Acta Cryst. (1976), B32, pag. 291-293, the geometric isomery has been definitely established by single crystal X-Ray diffraction.

Finally, in the publication "Analytical profiles of drug substances and excipients", vol. 25, (1998), page 85-121, in particular at page 99, it is stated that prior to 1976 the cis stereochemistry was assigned to the trans-isomer of Clomiphene (E-Chlomiphene), and only after the above publication on Acta Cryst. has the correct geometric isomery been definitively assigned.

These observations in the prior art have been confirmed by our experimentation. In particular, repeating the experiment 31 of U.S. Pat. No. 3,848,030, the trans-Clomiphene salt with racemic binaphthyl-phosphoric acid was isolated and not the salt with cis-Clomiphene as stated in said patent.

U.S. Pat. No. 2,914,563, in example 3, and the recent PCT application WO2014/031177, in example 1, disclose a process for the preparation of trans-Clomiphene citrate, containing from 30% to 50% of cis-Clomiphene, as citrate, by reaction of 1-p-(β-diethylaminoethoxy)phenyl]-1,2-diphenylethylene hydrochloride with N-chlorosuccinimmide in dry chloroform under reflux.

According to our experimental studies, these prior art methods for the preparation of Clomiphene and, in particular, trans-Clomiphene, suffer from drawbacks related to unknown impurities which can contaminate the final product Clomiphene.

SUMMARY OF THE INVENTION

The problem addressed by the present invention is therefore that of providing an improved process for the preparation of Clomiphene and, in particular trans-Clomiphene, and salts thereof which provides product with lower amounts of impurities.

This problem is solved by a process for the preparation of Clomiphene and salts thereof as outlined in the annexed claims, whose definitions are integral part of the present description.

Further features and advantages of the process according to the invention will result from the description hereafter reported of examples of realization of the invention, provided as an indication and not as a limitation of the invention.

DETAILED DESCRIPTION OF THE INVENTION

Figure 1:
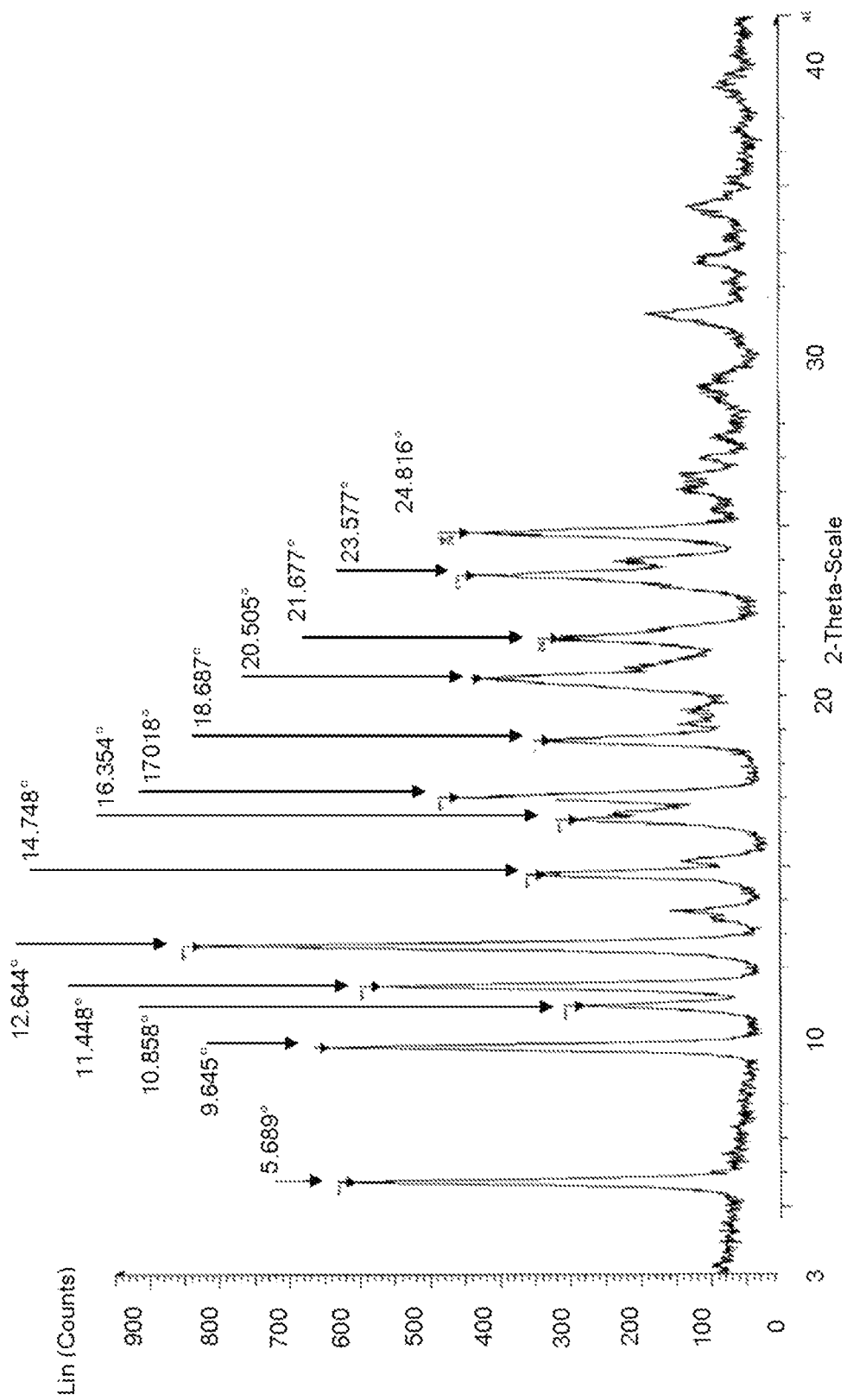
FIG. 1 shows the XPRD diffractogram of the solid form of trans-Clomiphene monocitrate.

One object of the present invention is to provide a process for the preparation of Clomiphene and salts thereof comprising the reaction of the mixture of geometric isomers of formula (V-E) and (V-Z) or salts thereof:

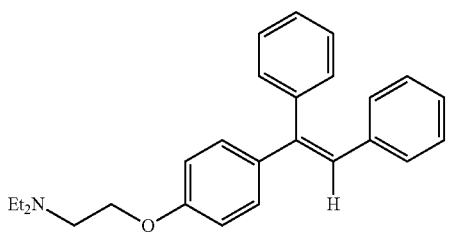 (V-E)

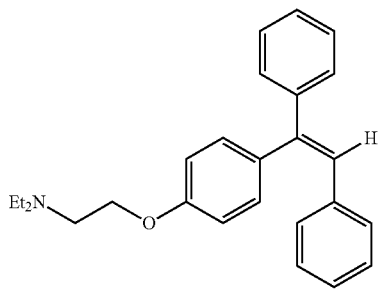 (V-Z)

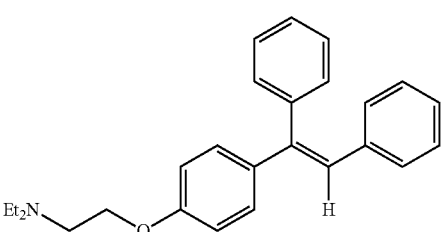 (V-E)

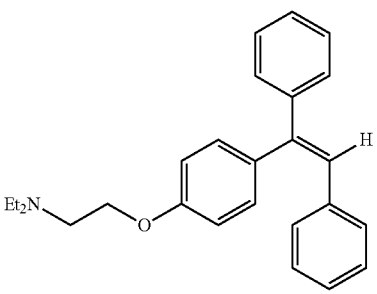 (V-Z)

in an organic solvent with a chlorinating agent, characterized in that the reaction is performed in presence of acetic acid or trifluoroacetic acid.

It has been surprisingly found that the prior art methods for the preparation of Clomiphene provide product containing two impurities, the first being trans-des-ethyl Chlomiphene, as monocitrate salt, having the following structure:

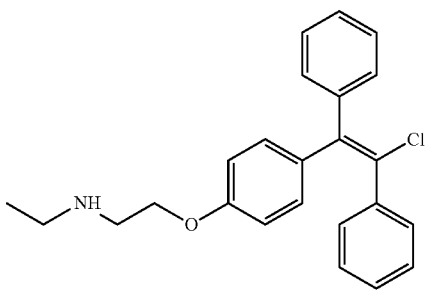 [SMILES: CCNCCOc1ccc(/C(=C(/Cl)c2ccccc2)c2ccccc2)cc1]

and the second being cis-des-ethyl Chlomiphene, as monocitrate salt, having the following structure:

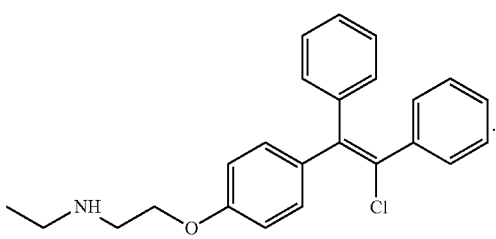 [SMILES: CCNCCOc1ccc(/C(=C(\Cl)c2ccccc2)c2ccccc2)cc1]

These impurities have relative retention times of 0.93 and 0.94 according to our analytical method (see example 10). According such analytical method these impurities have been found in amounts higher than 0.10%.

Moreover, it has been surprisingly found that both the impurities des-ethyl Clomiphene are generated during the chlorination reaction of the mixture of geometric isomers of formula (V-E) and (V-Z) or salts thereof:

with a chlorinating agent and, surprisingly, the formation of said impurities can be inhibited by the presence of acetic acid or trifluoroacetic acid in the reaction mixture.

The main effect provided by the presence of acetic acid or trifluoroacetic acid in the chlorination reaction mixture of the compounds of formula (V-E) and (V-Z) is thus to limit or to avoid the formation of the impurities cis and trans des-ethyl Clomiphene, thus allowing the preparation of Clomiphene with an amount of such impurities lower than 0.10%.

The analytical method described in Example 10 allows the identification and quantification of the impurities cis and trans des-ethyl Clomiphene into Chlomiphene.

Moreover, as additional effect, the presence of acetic acid or trifluoroacetic acid during the chlorination reaction of the compounds of formula (V-E) and (V-Z) shifts the ratio trans-Clomiphene / cis-Clomiphene from a range of 60-70: 40-30 to 75-85:25-15, thus favouring the preparation of trans-Clomiphene.

Furthermore, the presence of acetic acid or trifluoroacetic acid during the chlorination reaction of the compounds of formula (V-E) and (V-Z) provides the further effect of inhibiting the formation of chlorinated impurities such as the impurities named G and H of the European pharmacopeia being the two geometric isomers of the compound 2-[2-chloro-4-(2-chloro-1,2-diphenylethenyl)phenoxy]-N,N-diethylethanamine having the following structure:

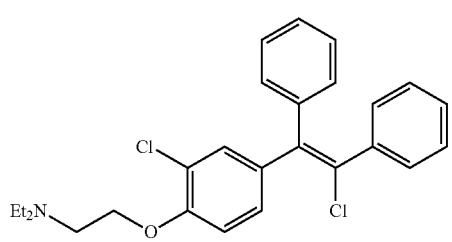

-continued

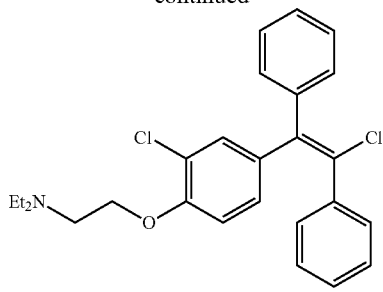

wherein the impurity G is the isomer having the higher-melting point while the impurity H is the isomer with lower-melting point.

The Clomiphene and salts prepared according to the process of the present invention are thus a mixture of trans-Clomiphene and cis-Clomiphene in ratio respectively from 75:25 to 99:1 and typically from 75:25 to 97:3.

The Clomiphene and salts prepared according to the process of the present invention include Clomiphene monocitrate, i.e. Clomiphene citrate (1:1), preferably Clomiphene in ratio trans-Clomiphene monocitrate/cis-Clomiphene monocitrate from 75:25 to 99:1.

The salts of the mixture of geometric isomers of formula (V-E) and (V-Z) can be salts with hydrochloric acid, hydrobromic acid, sulphuric acid, etc.

The preferred salt of the geometric isomers of formula (V-E) and (V-Z) is the hydrochloride salt.

The organic solvent of the process of the present invention can be a hydrocarbon solvent, a chlorinated solvent, acetate solvent, nitriles, etc.

An example of hydrocarbon solvent is toluene, while examples of chlorinated solvents are chloroform, dichloromethane, chlorobenzene, etc. and examples of acetates are isopropyl acetate or ethyl acetate, while an example of nitrile solvent is acetonitrile.

The chlorinating agent of the process of the present invention is a typical chlorinated solvent used in the organic chlorination reaction, such as, for example, dichlorodimethylhydantoin, N-Chlorosuccinimmide, trichloroisocianuric acid, etc.

According to a preferred embodiment, the process of the present invention is carried out with an amount of acetic acid or trifluoroacetic acid which is comprised between 1 and 3 volumes, more preferably about 2 volumes.

1 Volume means, for example, 1 mL per 1 gram or 1 liter per 1 Kilogram.

According to a preferred embodiment of the process of the present invention, the amount of organic solvent is comprised between 5 and 11 volumes, more preferably about 8 volumes.

According to a more preferred embodiment, the process of the present invention is carried out with an amount of acetic acid or trifluoroacetic acid which is comprised between 1 and 3 volumes and the amount of organic solvent is comprised between 5 and 11 volumes, again more preferably, an amount of acetic acid or trifluoroacetic acid is about 2 volumes and the amount of organic solvent is about 8 volumes.

According to a preferred embodiment, the process of the present invention is carried out using methylene chloride as organic solvent.

It has been found that methylene chloride provides a higher ratio trans-Clomiphene:cis-Clomiphene, increasing the ratio so that at the end of the chlorination reaction the ratio is comprised from 80:20 to 85:15.

Moreover, methylene chloride allows the chlorination reaction to be performed at lower temperatures, for example at 25° C., while toluene, for example requires 60° C. Performing the reaction at lower temperatures avoids the need to use a large excess of chlorination agent, which is partially degraded operating at high temperatures. Thus, using methylene chloride as organic solvent to perform the chlorination reaction, the advantage of reducing the amount of chlorination agent employed is achieved.

Moreover, it has been noticed that when the chlorination reaction of the compounds of formula (V-E) and (V-Z) is carried out in the mixture of dichloromethane and acetic acid or trifluoroacetic acid, the highest ratio of trans-Clomiphene:cis-Clomiphene is achieved, so that such process can be seen as a process for the preparation of trans-Clomiphene.

According to a preferred embodiment of the process of the present invention, the amount of methylene chloride is comprised between 5 and 11 volumes, more preferably about 8 volumes.

According to a preferred embodiment of the process of the present invention, the amount of acetic acid or trifluoroacetic acid is comprised between 1 and 3 volumes and the amount of methylene chloride is comprised between 5 and 11 volumes, more preferably is about 8 volumes.

According to a preferred embodiment of the process of the present invention, the amount of acetic acid or trifluoroacetic acid is about 2 volumes and the amount of methylene chloride is about 8 volumes.

According to a preferred embodiment of the process of the present invention, the reaction is performed at a temperature between 0° C. and 80° C., more preferably between 20° C. and 40° C., or at about 25° C. When the reaction is carried out at about 25° C., a large excess of chlorination reagent to complete the reaction it is not required.

According to a preferred embodiment of the process of the present invention, the amount of chlorinating agent is comprised in the range from 0.45 to 0.60 molecular equivalents, preferably from 0.48 to 0.52 mol. equivalents, again more preferably, about 0.51 mol. equivalents.

According to a preferred embodiment of the process of the present invention, the chlorinating agent is dichlorodimethylhydantoin since it is the chlorination agent that provides the best impurity profile.

According to a preferred embodiment of the process of the present invention, the reaction is carried out under anhydrous conditions. It has been found that the presence of moisture or water is detrimental for the chlorination reaction since the presence of water provide the products containing the Impurity C of the European Pharmacopeia having the following structure:

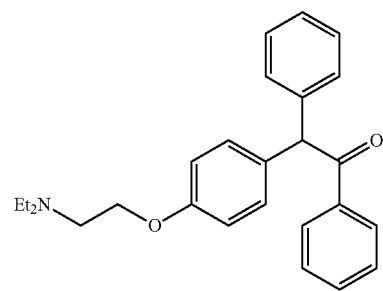

and the chloridrine impurity, as a mixture of two isomers, having the following structure:

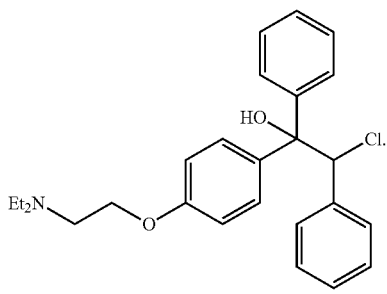

According to a preferred embodiment of the process of the present invention the amount of water should be lower than 500 ppm in the chlorination reaction mixture so that the amount both impurity C and chloridrine impurities are each lower than 0.10% in the final product Clomiphene.

According to a more preferred embodiment of the process of the present invention the amount of water should be lower than 250 ppm in the chlorination reaction mixture.

The molar yield of the process according to the present invention is comprised between 92% and 96%, being typically about 94%.

The product Clomiphene prepared according to the process of the present invention contains less than 0.06% of each impurity des-ethyl Chlomiphene and less than 0.06% of impurities G and H according to the European Pharmacopoeia.

The process of the present invention, optionally, further comprises the step of preparation of the compound of formula (VI):

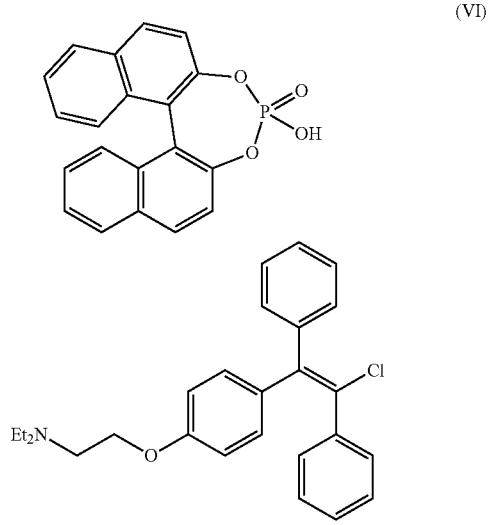

(VI)

by addition of racemic binaphthyl-phosphoric acid to the reaction mixture at the end of the chlorination reaction.

In particular, at the end of the chlorination reaction, racemic binaphthyl-phosphoric acid, i.e. the (±)-1,1'-Binaphthyl-2,2'-diyl hydrogen phosphate, can be added to the reaction mixture thus carrying out the whole process one-pot.

Also single enantiomer of the binaphtyl-phosphoric acid, i.e. the (+)-1,1-Binaphthyl-2,2'-diyl hydrogen phosphate or (+1,1'-Binaphthyl-2,2'-diyl hydrogen phosphate can be added at the end of the chlorination reaction achieving substantially the same results obtained using the racemic form, which is the one economically more advantageous.

The addition of racemic binaphthyl-phosphoric acid to the reaction mixture causes the precipitation of the salt of trans-clomiphene with racemic binaphthyl-phosphoric acid. Such salt shows a ratio trans-clomiphene/cis-clomiphene from 90:10 to 98:2 (see examples 3a-3d).

The salt of trans-clomiphene with racemic binaphthyl-phosphoric acid can be optionally further purified by preparation of the trans-clomiphene base and re-precipitating the salt of trans-clomiphene with racemic binaphthyl-phosphoric acid by addition of racemic binaphthyl-phosphoric acid to the trans-clomiphene base in an organic solvent. Such salt of trans-Clomiphene contains less than 0.15% (HPLC A% of the Cis-Clomiphene) (see examples 4a-4c).

Figure 5:
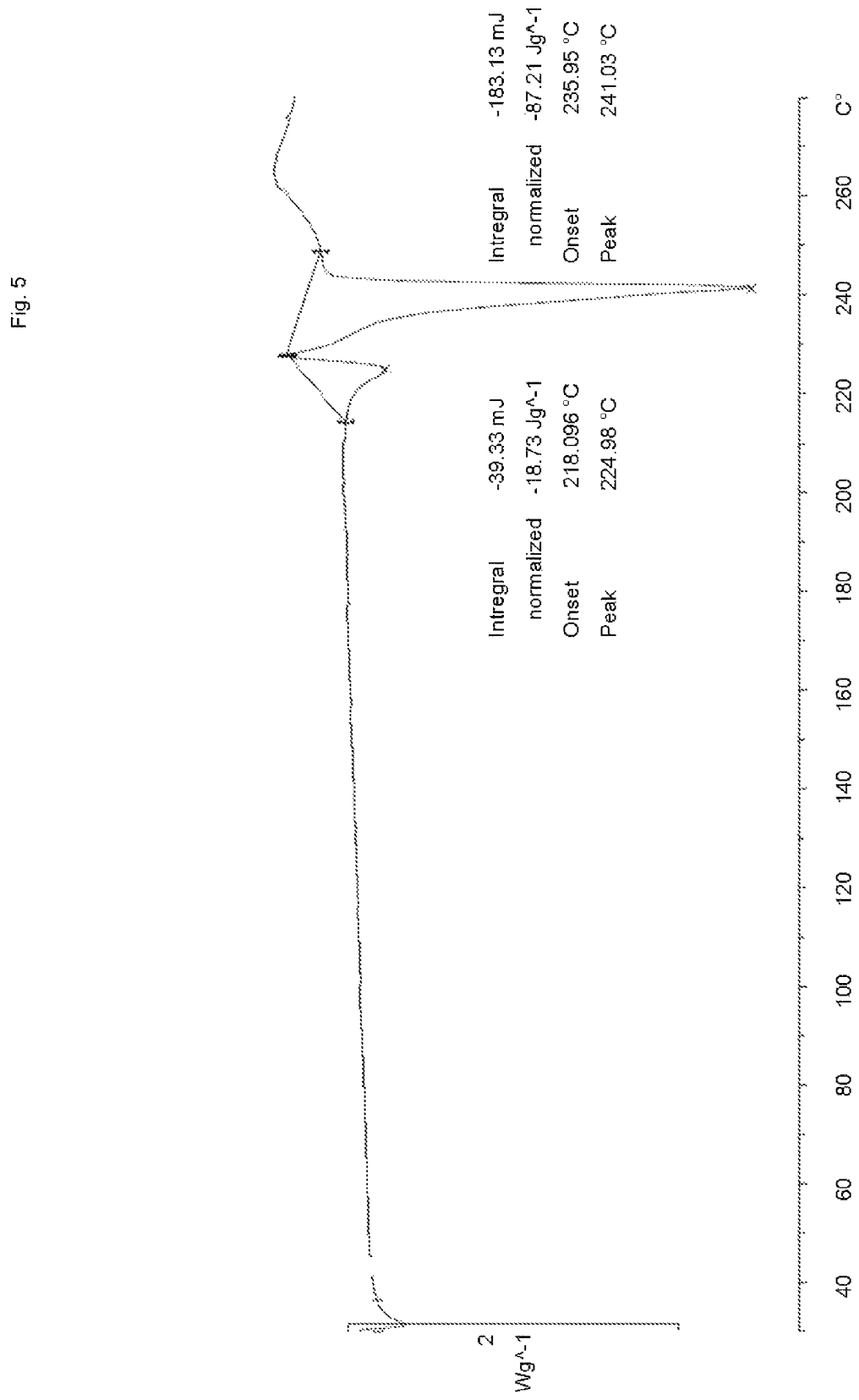
FIG. 5 shows the DSC curve of trans-Clomiphene salt with racemic binaphthyl-phosphoric acid of formula (VI).

The salt of trans-clomiphene with racemic binaphthyl-phosphoric acid shows a melting point of 218° C. as determined by DSC on set point (see example 5 and FIG. 5). The trans configuration has been confirmed by 2D-NMR analysis. This experimental melting point is substantially the same of that disclosed in Example 31 of U.S. Pat. No. 3,848,030 (220-222° C.), thus confirming the wrong assignation of the geometric isomerism in said document and confirming that the salt of trans-clomiphene with racemic binaphthyl-phosphoric acid is already known since 70's, including the polymorphic solid form isolated from methanol having m.p. 220-222° C.

The salt of trans-clomiphene with racemic binaphthyl-phosphoric acid, optionally purified or not, according to the teaching of the previous paragraph, can be converted in the trans-Clomiphene free base according to the teaching of U.S. Pat. No. 3,848,030 and then converted to the trans-Clomiphene monocitrate salt by addition of citric acid in acetone. The trans-Clomiphene monocitrate salt thus prepared contains less than 0.4% of Cis-Clomiphene (HPLC A/A%) (see examples 6a-6c, 7), in particular from 0.40% to 0.04% of cis-Clomiphene.

The process of the present invention can further comprise the step of preparation of the mixture of geometric isomers of formula (V-E) and (V-Z) or salts thereof:

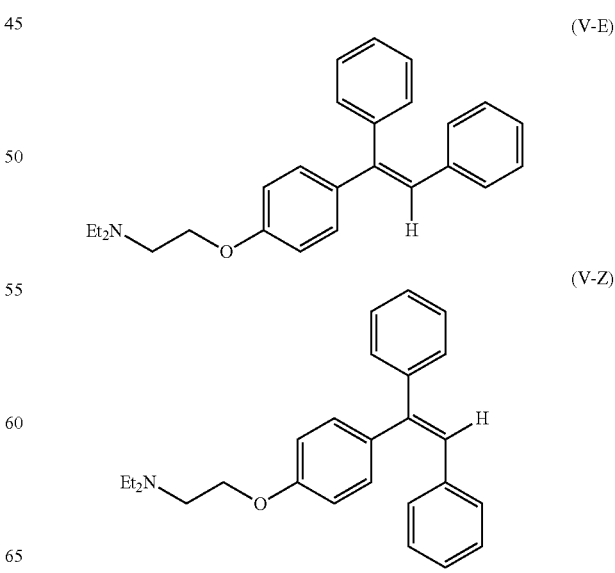

by dehydration reaction of the compound of formula (VII):

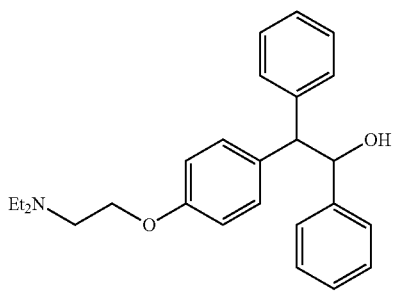
(VII)

The dehydration reaction of the compound of formula (VII) is typically carried out in an organic solvent in presence of an acid.

The dehydration reaction is preferably carried out with hydrochloric acid in

Toluene. Therefore, the compounds of formula (V-E) and (V-Z) of the present invention are typically in form of hydrochloride salts.

Since the process of the present invention provides Clomiphene having a ratio of trans-Clomiphene and cis-Clomiphene well in favor of the trans-Clomiphene, the process of the present invention can be seen as a process for the preparation of trans-Clomiphene.

Thus, the present invention also relates to a process for the preparation of trans-Clomiphene and salts thereof comprising the reaction of the mixture of geometric isomers of formula (V-E) and (V-Z) or salts thereof:

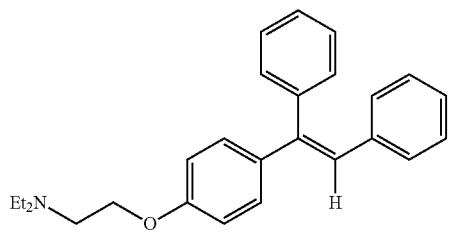
(V-E)

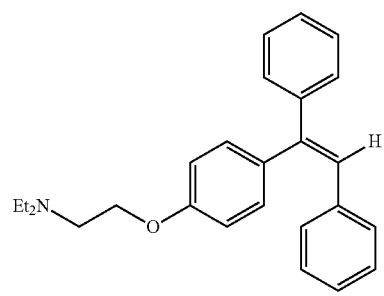
(V-Z)

in an organic solvent with a chlorinating agent, characterized in that the organic solvent is methylene chloride and the reaction is performed in presence of acetic acid or trifluoroacetic acid.

The combination of methylene chloride as solvent and the presence of acetic acid or trifluoroacetic acid in the chlorination reaction of the mixture of geometric isomers of formula (V-E) and (V-Z) or salts thereof, provides the higher ratio trans-Clomiphene versus cis-Clomiphene, so that this combination of features is well suitable for a process for the preparation of trans-Clomiphene.

The process according to the present invention preferably provides Clomiphene as a mixture of trans-Clomiphene and cis-Clomiphene in ratio from 75:25 to 99:1.

Acetic acid or trifluoroacetic acid can therefore be conveniently used to carry out the chlorination reaction with a chlorinating agent of the mixture of geometric isomers of formula (V-E) and (V-Z) or salts thereof:

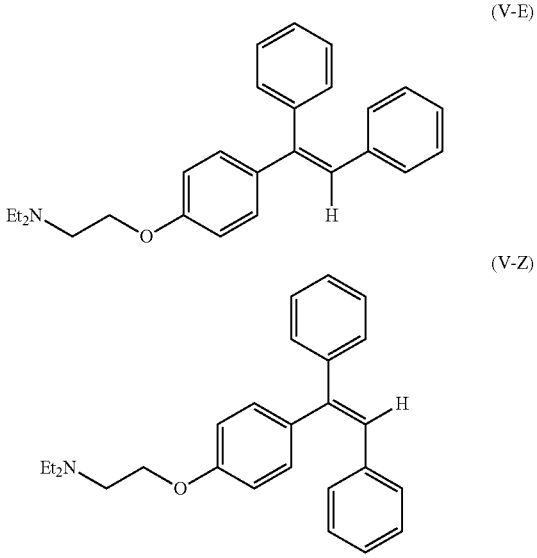

to provide Clomiphene and salts thereof.

The process of the present invention can be carried out with any one of the combinations of preferred embodiments above described.

During the development of the process for the preparation of trans-Clomiphene a stable solid form of trans-Clomiphene monocitrate has been surprisingly discovered.

The term monocitrate means 1 mole of citric acid for 1 mole of trans-Clomiphene. Thus, trans-Clomiphene monocitrate can also be named trans-Clomiphene citrate (1:1) or Enclomifene citrate (1:1).

In particular, it has been found a process for the preparation of a solid form of trans-Clomiphene monocitrate of formula:

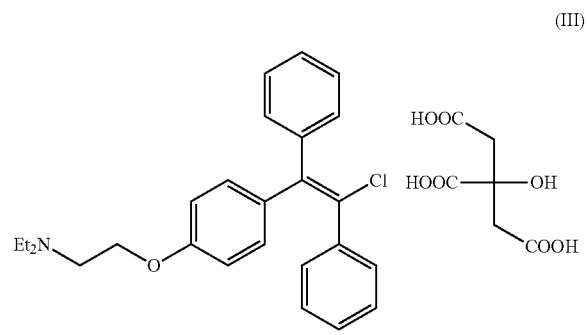
(III)

by treatment of trans-Clomiphene in an organic solvent with citric acid monohydrate.

The following scheme shows the process for the preparation of a solid form of Trans-Clomiphene monocitrate:

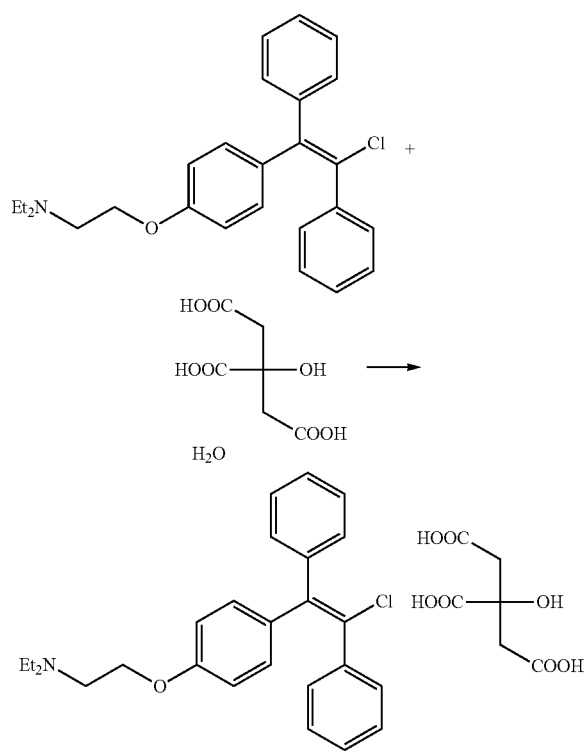

The organic solvent to carry out such a process is a ketone solvent such as for example acetone or methylethylketone or an acetate solvent such as ethylacetate or isopropylacetate, acetone being preferred.

Figure 2:
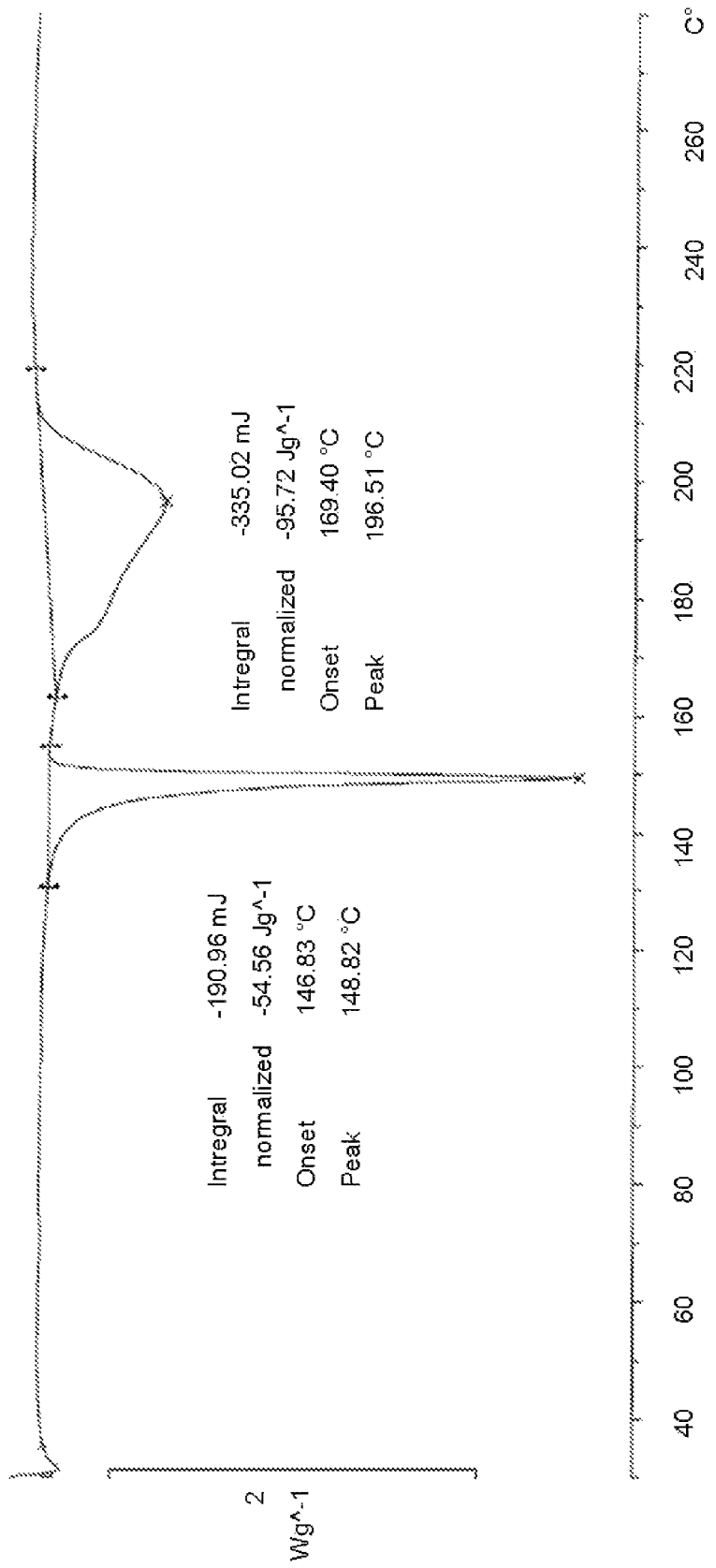
FIG. 2 shows the DSC curve of the solid form of trans-Clomiphene monocitrate.
Figure 3:
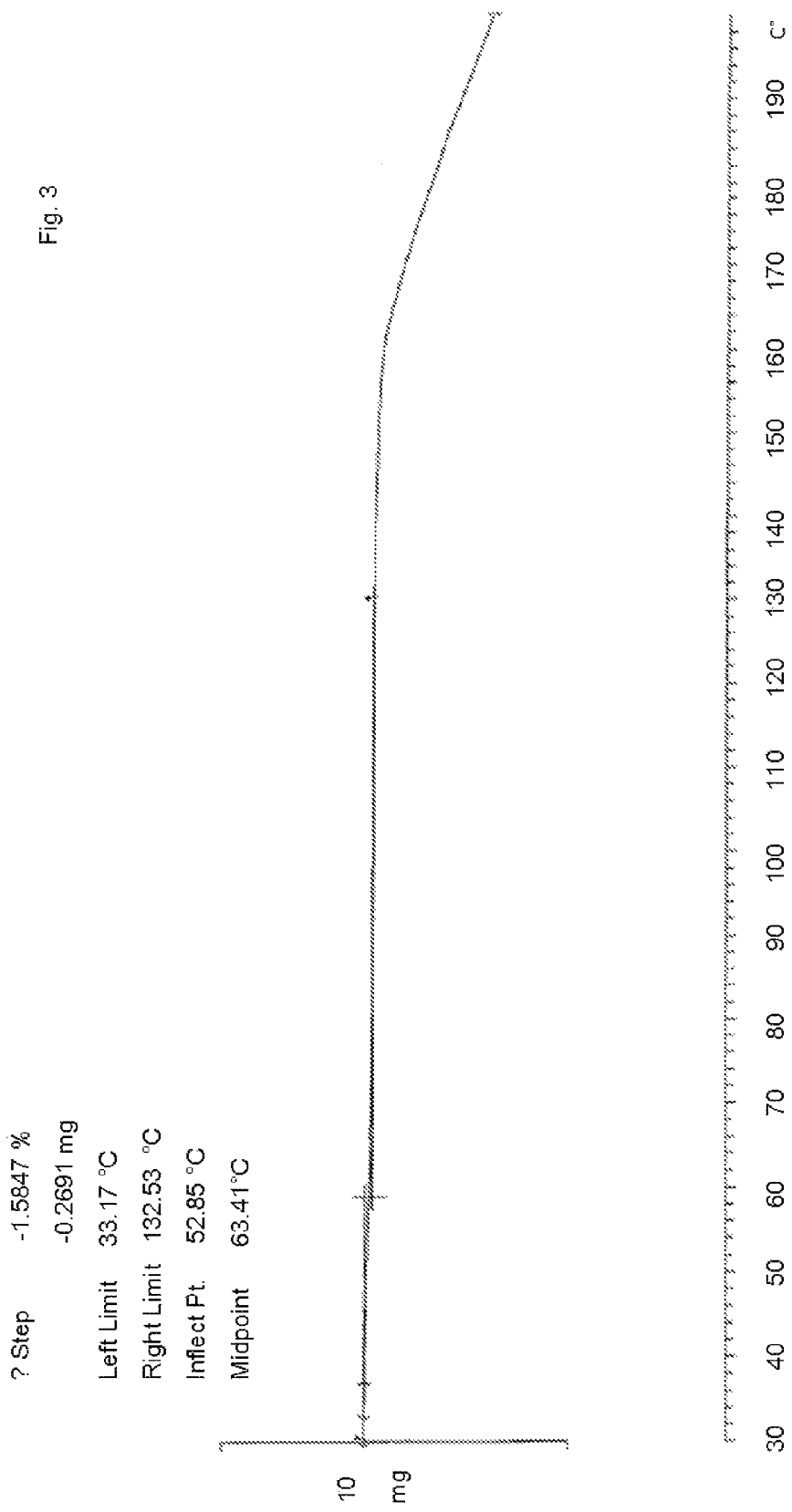
FIG. 3 shows the TGA curve of the solid form of trans-Clomiphene monocitrate.

The solid form of trans-Clomiphene monocitrate obtained by such process has a melting point of about 147° C. as measured by DSC (onset) (See FIG. 2).

The solid form of trans-Clomiphene monocitrate obtained by such process exhibits a characteristic X-ray powder diffraction pattern with characteristic peaks expressed in 2-Theta values (2θ): 5.69 (s), 9.64 (s), 10.86 (m), 11.45 (s), 12.64 (vs), 14.75 (m), 16.35 (m), 17.02 (m), 18.69 (m), 20.51 (m), 21.68 (m), 23.58 (m), 24.82 (m), 31.2 (w); wherein (vs)=very strong intensity; (m)=medium intensity; (w)=weak intensity.

The solid form of trans-Clomiphene monocitrate exhibits a characteristic X-ray powder diffraction pattern with stronger characteristic peaks expressed in 2-Theta values (2θ) at: 5.69 (s), 9.64 (s), 11.45 (s), 12.64 (vs).

The solid form of trans-Clomiphene monocitrate obtained by such process is a crystalline solid.

The solid form of trans-Clomiphene monocitrate obtained by such process has non-needle-shaped crystal.

The solid form of trans-Clomiphene monocitrate obtained by such process has a melting point of about 147° C. Said melting point is well different from that disclosed in literature for the trans-Clomiphene monocitrate obtained using anhydrous citric acid in Ethanol and as disclosed in example 31 of U.S. Pat. No. 3,848,030, being 133-135° C.

By comparison of the melting points it appears that the solid form of trans-Clomiphene monocitrate of the present invention prepared using citric acid monohydrate is different from the known solid form of anhydrous trans-Clomiphene prepared using anhydrous citric acid, and, it appears that the solid form of the invention is thermodynamically more stable than the known form since it has higher melting point.

It has been found that reacting trans-Clomiphene with citric acid monohydrate in an organic solvent, a new solid form of Trans-Clomiphene monocitrate, maybe an hydrate form, (for example an hydrate having stoichiometry ratio of Trans-Clomiphene/citric acid/water of 3:3:2), is obtained by such process and said form is particularly stable toward the humidity, i.e. it does not show hygroscopic phenomena.

The solid form of trans-Clomiphene monocitrate obtained by such process shows a Karl Fischer (K.F.) value of about 2.0%.

The solid form of trans-Clomiphene monocitrate of the invention can be prepared dissolving trans-Clomiphene in an organic solvent and adding citric acid monohydrate.

When trans-Clomiphene is dissolved in an organic solvent and anhydrous citric acid is added, then trans-Clomiphene monocitrate as anhydrous form is prepared (see example 7).

According to a preferred embodiment, the organic solvent for the preparation of the solid form of trans-Clomiphene monocitrate is acetone.

According to a preferred embodiment, the process for the preparation of the solid form of trans-Clomiphene monocitrate is carried out at temperature comprised between 20° C. and 100° C., preferably between 40° C. and 60° C., more preferably at about 50° C.

According to a preferred embodiment, the process for the preparation of the solid form of trans-Clomiphene monocitrate is carried out adding citric acid monohydrate, as solid or in solution of an organic solvent, to a solution of trans-Clomiphene in an organic solvent.

According to a preferred embodiment of the process for the preparation of the solid form of trans-Clomiphene monocitrate, the amount of citric acid monohydrate used is comprised between 1.1 and 1.3 mol. equivalents.

According to a preferred embodiment of the process for the preparation of the solid form of trans-Clomiphene citrate, the starting material trans-Clomiphene comprises less than 5% (HPLC A%) of cis-Clomiphene, preferably less than 2% cis-Clomiphene.

The process of the present invention for the preparation of the solid form of trans-Clomiphene monocitrate can be carried out with any one of the combinations of preferred embodiments above described.

Thus, citric acid monohydrate can be used for the preparation of the solid form of trans-Clomiphene monocitrate according to the process of the present invention.

Pharmaceutical compositions comprising the solid form of trans-Clomiphene monocitrate according to the present invention can be prepared according to the teaching of example 3 of WO2014/031177A1.

Therefore, the solid form of trans-Clomiphene monocitrate of the present invention can be used in medicine, in particular, can be used for the treatment ovulatory dysfunction or polycystic ovary syndrome.

Experimental Section

The starting material 1-{4-[2-(Diethylamino)ethoxy]phenyl}-1,2-diphenylethanol can be prepared according to well-known prior art methods or can be purchased on the market.

Example 1

Preparation of Clomiphene Citrate from 1-{4-[2-(Diethylamino)ethoxy]phenyl}-1,2-diphenylethanol

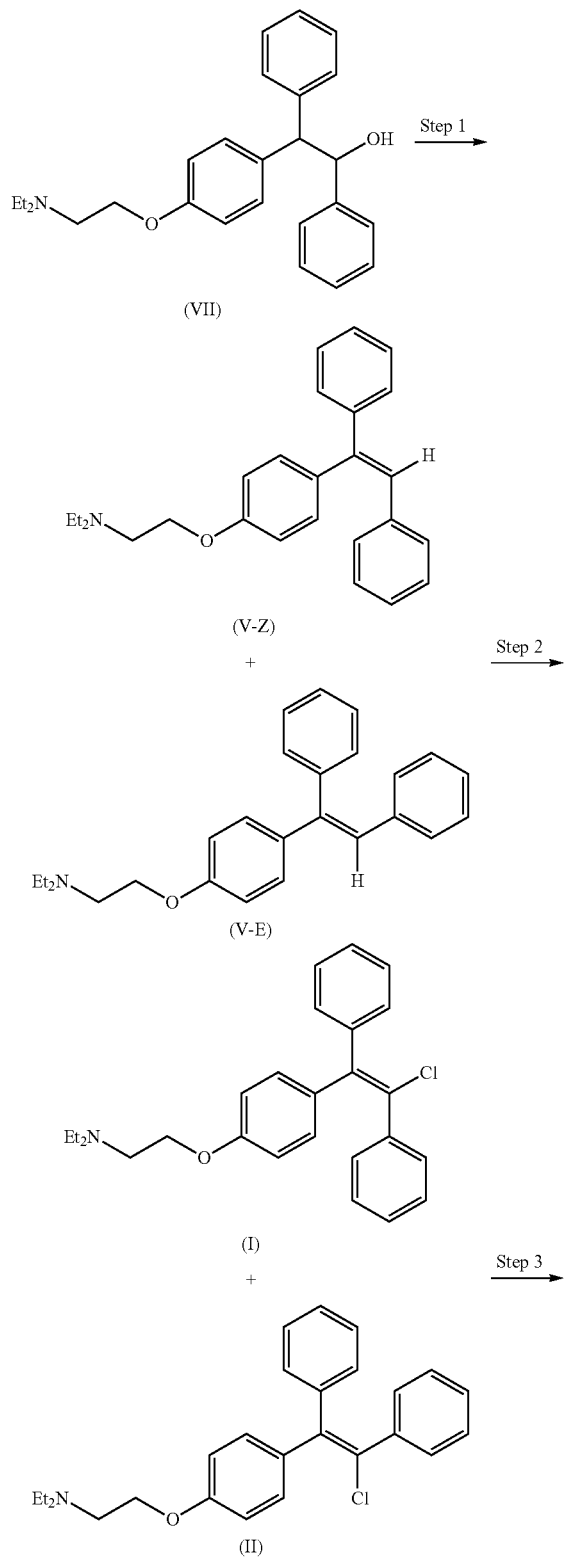

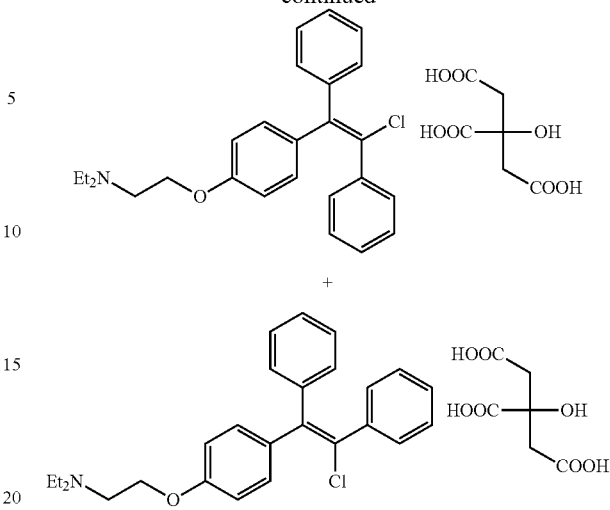

Step 1

A round bottomed flask fitted with distillation equipment was loaded with 250 g of 1-{4-[2-(Diethylamino)ethoxy]phenyl}-1,2-diphenylethanol and 1250 mL of toluene. To this mixture, 85 mL of HCl 32% w/w were added, the temperature was raised to the boiling point and all the water was azeotropically removed by means of a Dean-Stark apparatus, obtaining 2-{4-[(E/Z)-1,2-diphenylethenyl]phenoxy}-N,N-diethylethanamine hydrochloride, as mixture of geometric isomers of formula (V-Z) and (V-E).

Step 2

The reaction mixture was brought to 60° C. and, maintaining this temperature, 500 mL of acetic acid were added during 30'. The water content was checked below 500 ppm (Karl Fischer titration).

A warm solution (50-60° C.), prepared with 60 g of dichloro dimethyl hydantoin (1,3-dichloro-5,5-dimethyl hydantoin; abbreviated DCDMI) (0.474 mol. equiv.) in 600 mL of toluene, was slowly added to the reaction mixture during 90' maintaining the temperature at about 60° C. After checking the conversion by HPLC, a small addition of DCDMI solution was necessary in order to have the starting material below 0.5%. The reaction mixture was cooled to 15-20° C. and treated slowly with 750 mL of water and, up to pH 12, approximately 1000 mL of aqueous sodium hydroxide 30% w/w solution. After stirring for 30', the layers were separated and the organic phase was washed with 3×250 mL of water and concentrated by vacuum distillation thus obtaining 280 g of Clomiphene, as an oil containing some residual toluene of formula (I) and (II).

Step 3

The oil obtained in the previous step was taken up with 625 mL of acetone, the clear solution warmed to gentle boiling and a solution composed of 142.5 g of citric acid monohydrate and 1000 mL of acetone was slowly added during 30'. The reaction mixture was stirred while slowly cooling to 0° C. and then 4 hours at 0° C. The product was filtered, washed with acetone and dried under vacuum obtaining 361 g of Clomiphene citrate, the molar yield was 94.1%. HPLC purity >98% (A/A%).

Example 2a

Preparation of Salt of Trans-Clomiphene with Racemic Binaphthyl-Phosphoric Acid, Starting From Clomiphene Citrate

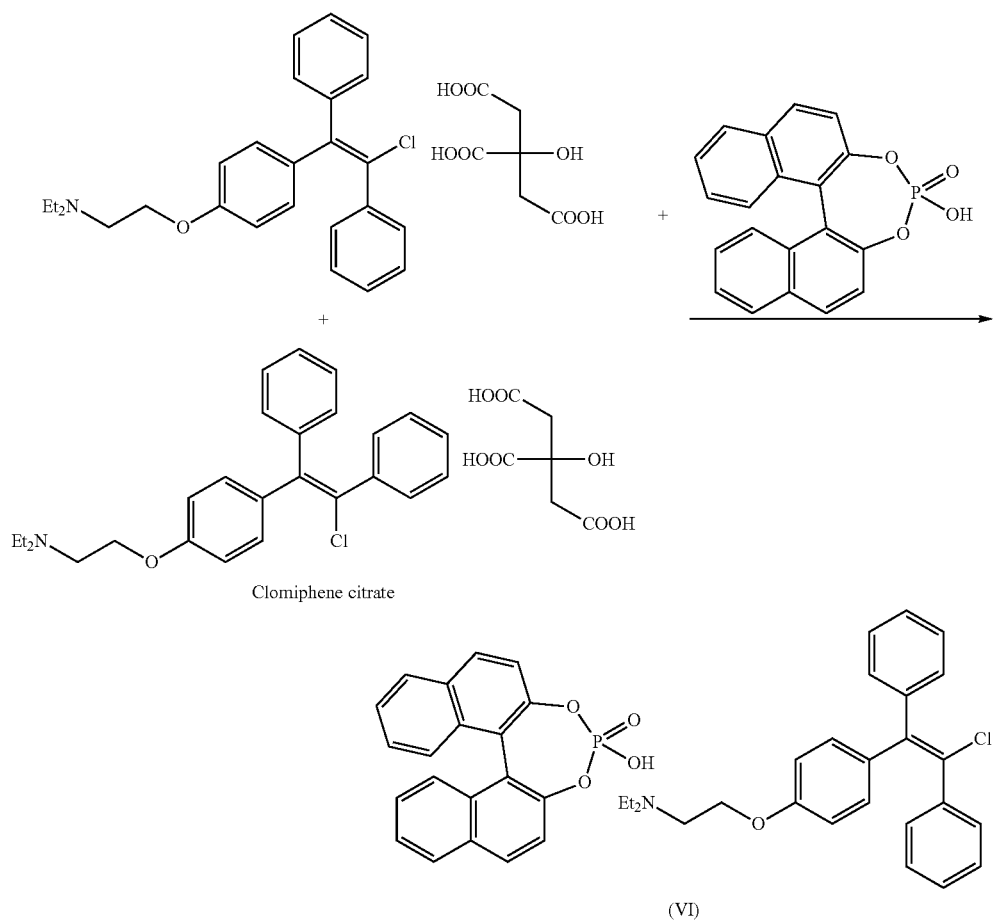

Clomiphene citrate (VI)

A round bottom flask was charged 100 gr of Clomiphene Citrate (HPLC analysis (A/A%): 65.21% E-Clomiphene, 34.06% Z-Clomiphene) and 1000 mL of Methanol. The suspension was stirred at 30° C. up the complete dissolution. Then a solution of racemic binaphthyl-phosphoric acid (abbreviated BPA) 30 gr (0.515 eq) in 30 mL of DMF was added. At the end of addition the mixture was stirred for 1 hour at 30° C. The obtained suspension was filtered and the solid was washed with 100 mL of Methanol.

50.4 gr of E-Clomiphene BPA salt were obtained.

HPLC Analysis (A/A%): 97.04% E-Chlomiphene, 2.5% Z-Clomiphene.

Example 2b

Preparation of Salt of Trans-Clomiphene With Racemic Binaphthyl-Phosphoric Acid, Starting From Clomiphene Citrate

A round bottom flask was charged 50 gr of Clomiphene Citrate (the same as that used in example 2a) and 500 mL of Methanol. The suspension was heated at 40-45° C. and stirred up to the complete dissolution. Then a solution of BPA 15 gr (0.515 eq) in 300 mL of methanol was added. At the end of addition the mixture was stirred for 1 hour at 20° C. The obtained suspension was filtered and the solid was washed with 100 mL of Methanol.

24.1 gr of E-Clomiphene BPA salt were obtained.

HPLC Analysis (A/A%): 98.96% E-Chlomiphene, 0.69% Z-Clomiphene.

Example 2c

Preparation of Salt of Trans-Clomiphene With Racemic Binaphthyl-Phosphoric Acid, Starting From Clomiphene Citrate

In a round bottom flask was charged 100 gr of Clomiphene Citrate (the same as that used in example 2a) and 1000 mL of Methanol. The suspension was heated at 40-45° C. and stirred up the complete dissolution. Then a solution of BPA 30 gr (0.515 eq) in 1000 mL of methanol was added. At the end of addition the mixture was stirred for 1 hour at 20° C. the obtained suspension was filtered and the solid was washed with 100 mL of Methanol.

47.9 gr of E-Clomiphene BPA salt were obtained.

HPLC Analysis (A/A%): 98.81% E-Clomiphene, 0.79% Z-Clomiphene.

Example 2d

Preparation of Salt of Trans-Clomiphene With Racemic Binaphthyl-Phosphoric, Starting From Clomiphene Citrate

In a round bottom flask was charged 150 gr of Clomiphene Citrate (the same as that used in example 2a) and 1500 mL of Methanol. The suspension was heater at 40-45° C. and stirred up the complete dissolution. Then a solution of BPA 45 gr (0.515 eq) in 900 mL of methanol was added. At the end of addition the mixture was stirred for 1 hour at 20° C. The obtained suspension was filtered and the solid was washed with 100 mL of methanol.

76.4 gr of E-Clomiphene BPA salt were obtained.

HPLC Analysis (A/A%): 98.82% E-Chlomiphene, 0.80% Z-Clomiphene.

Example 3a

Preparation of Salt of Trans-Clomiphene With Racemic Binaphthyl-Phosphoric Acid, Starting From 1-{4-[2-(Diethylamino)-ethoxy]phenyl}-1,2-diphenylethanol

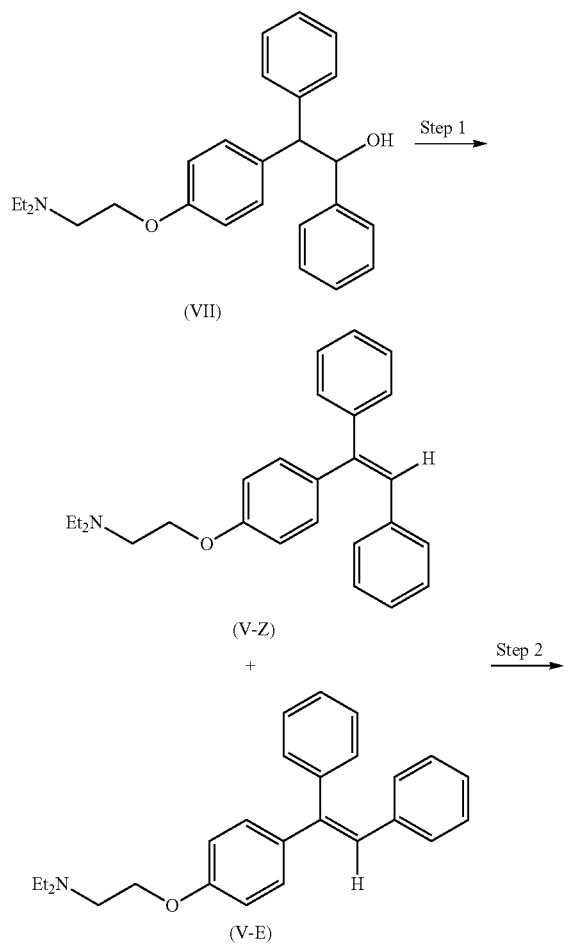

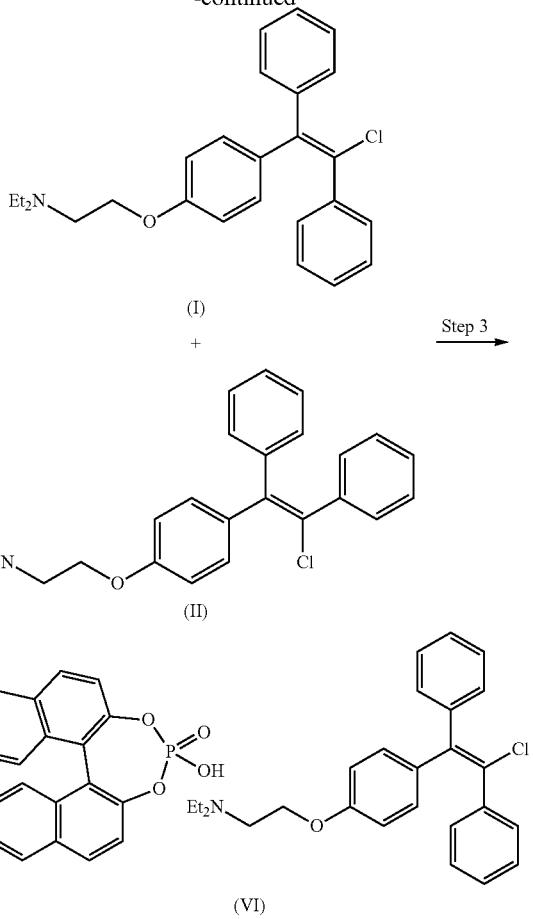

In a round bottom flask was charged 100 gr of 1-{4-[2-(Diethylamino)ethoxy]phenyl}-1,2-diphenylethanol of formula (VII), 300 mL of Toluene and 62 mL of HCl sol. 32%. The mixture was stirred at T=35-40° C. for 30 minutes. Then the solution was concentrated to residual and the residue was diluted with 300 mL of Toluene. The organic solution was concentrated to residual and the residue was diluted with 800 mL of Dichloromethane (abbreviated DCM). Acetic acid (200 mL) was added to the solution and a solution of DCDMI 26 gr in 250 mL of DCM was added in a period of 90 minutes. At the end of addition the mixture was stirred for 2 hours at room temperature. The obtained solution was added in a second round bottom flask containing a solution of 400 mL NaOH 30% and 300 mL of water. The mixture was stirred for 1 hour then the phases were separated and the organic phase was washed five times with water (5×100 mL). The obtained organic phase was concentrated to residual and the residue was diluted with 500 mL of Methanol. A solution of racemic binaphthyl-phosphoric acid 45 gr in 1000 mL was added at T=30° C. The obtained solution was stirred at r.t. (room temperature) for 1 hour. The suspension was filtered and the solid was washed with 100 mL of Methanol.

79.7 gr of E-Clomiphene salt with racemic binaphthyl-phosphoric acid were obtained.

HPLC Analysis (A/A%): 97.70% E-Clomiphene, 1.67% Z-Clomiphene.

Example 3b

Preparation of Salt of Trans-Clomiphene With Racemic Binaphthyl-Phosphoric Acid

In a round bottom flask was charged 100 gr of 1-{4-[2-(Diethylamino)ethoxy]phenyl}-1,2-diphenylethanol of formula (VII), 300 mL of Toluene and 62 mL of HCl sol. 32%. The mixture was stirred at T=35-40° C. for 30 min. then the solution was concentrated to residual and the residue was diluted with 300 mL of Toluene. The organic solution was concentrated to residual and the residue was diluted with 800 mL of DCM. The organic solution was concentrated to residual and the residue was diluted with 300 mL of Toluene. The organic solution was concentrated to residual and the residue was diluted with 800 mL of DCM. Acetic acid (200 mL) was added to the solution and a solution of DCDMI 26 gr in 250 mL of DCM was added in a period of 90 min. At the end of addition the mixture was stirred for 2 hours at r.t. The obtained solution was added in a second round bottom flask containing a solution of 400 mL NaOH 30% and 300 mL of water. The mixture was stirred for 1 hour then the phase were separated and the organic phase was washed five times with water (5×100 mL). The obtained organic solution was concentrated to residual and the residue was diluted with 500 mL of Methanol. A solution of racemic binaphthyl-phosphoric acid (abbreviated BPA) 45 gr in 700 mL was added at T=30° C. The obtained solution was stirred at r.t. for 1 hour. The suspension was filtered and the solid was washed with 100 mL of Methanol.

90 gr of E-Clomiphene BPA salt were obtained.

HPLC Analysis (A/A%): 94.49% E-Clomiphene, 4.15% Z-Clomiphene.

Example 3c

Preparation of Salt of Trans-Clomiphene With Racemic Binaphthyl-Phosphoric Acid

In a round bottom flask was charged 100 gr of 1-{4-[2-(Diethylamino)ethoxy]phenyl}-1,2-diphenylethanol of formula (VII), 300 mL of Toluene and 62 mL of HCl sol. 32%. The mixture was stirred at T=35-40° C. for 30' then the solution was concentrated to residual and the residue was diluted with 300 mL of Toluene. The organic solution was concentrated to residual and the residue was diluted with 300 mL of Toluene. The organic solution was concentrated to residual and the residue was diluted with 800 mL of DCM. Acetic acid (200 mL) was added to the solution and a solution of DCDMI 26 gr in 250 mL of DCM was added in a period of 90'. At the end of addition the mixture was stirred for 2 hours at r.t. The obtained solution was added in a second round bottom flask containing a solution of 400 mL NaOH 30% and 300 mL of water. The mixture was stirred pro 1 hour then the phase was spitted an the organic phase was washed five times with water (5×100 mL). The obtained organic solution was concentrated to residual and the residue was diluted with 500 mL of Methanol. A solution of racemic binaphthyl-phosphoric acid (abbreviated BPA) 45 gr in 1000 mL was added at T=30° C. The obtained solution was stirred at r.t. for 1 hour. The suspension was filtered and the solid was washed with 100 mL of Methanol.

78.3 gr of E-Clomiphene BPA salt were obtained.

HPLC Analysis (A/A%): 96.53% E-Clomiphene, 1.51% Z-Clomiphene.

Example 3d

Preparation of Salt of Trans-Clomiphene With Racemic Binaphthyl-Phosphoric Acid

In a round bottom flask was charged 100 gr of 1-{4-[2-(Diethylamino)ethoxy]phenyl}-1,2-diphenylethanol of formula (VII), 300 mL of Toluene and 62 mL of HCl sol. 32%. The mixture was stirred at T=35-40° C. for 30' then the solution was concentrated to residual and the residue was diluted with 300 mL of Toluene. The organic solution was concentrated to residual and the residue was diluted with 300 mL of Toluene. The organic solution was concentrated to residual and the residue was diluted with 300 mL of Toluene. The organic solution was concentrated to residual and the residue was diluted with 800 mL of DCM. Acetic acid (200 mL) was added to the solution and a solution of DCDMI 26 gr in 250 mL of DCM was added in a period of 90'. At the end of addition the mixture was stirred for 2 hours at r.t. The obtained solution was added in a second round bottom flask containing a solution of 400 mL NaOH 30% and 300 mL of water. The mixture was stirred for 1 hour then the phase was spitted an the organic phase was washed five times with water (5×100 mL). The obtained organic solution was concentrated to residual and the residue was diluted with 1000 mL of Methanol. A solution of BPA 72 gr. in 1000 mL was added at T=30° C. The obtained solution was stirred at r.t. for 1 hour. The suspension was filtered and the solid was washed with 100 mL of Methanol.

119.1 gr of E-Clomiphene BPA salt were obtained.

HPLC Analysis (A/A%): 95.97% E-Chlomiphene, 3.39% Z-Clomiphene.

Example 4a

Purification of the Trans-Clomiphene Salt With Racemic Binaphthyl-Phosphoric Acid of Formula (VI)

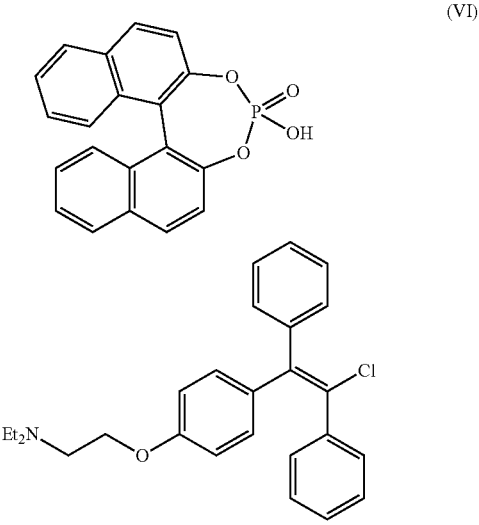

In a round bottom flask was charged 100 gr of E-Clomiphene BPA salt of formula (VI) (HPLC A/A%: 99.31% E-Clomiphene, 0.51% Z-Clomiphene) and 600 mL of Toluene. The suspension was stirred at r.t. and then 24 mL of NaOH 30% were added. Then the obtained suspension was filtered and the obtained solution was washed with 250 mL of water. The organic solution was concentrate to residual and the residue was diluted with 800 mL of Methanol. A solution of racemic binaphthyl-phosphoric acid (abbreviated BPA) 32 gr (0.515 eq) in 800 mL of Methanol was added. At the end of addition the mixture was stirred for 1 hour at 30° C. the obtained suspension was filtered and the solid was wash with 100 mL of Methanol.

57.1 gr of E-Clomiphene BPA salt of formula (VI) were obtained.

HPLC Analysis (A/A%): 99.11% E-Chlomiphene, 0.03% Z-Clomiphene.

Example 4b

Purification of Trans-Clomiphene Salt with Racemic Binaphthyl-Phosphoric Acid of Formula (VI)

In a round bottom flask was charged 114 gr of E-Clomiphene BPA salt (HPLC A/A%: 99.43% E-Clomiphene, 0.35% Z-Clomiphene) and 790 mL of Toluene. The suspension was stirred at r.t. and then 28 mL of NaOH 30% were added. Then the obtained suspension was stirred for 2 hours then was filtered and the obtained solution was washed with 290 mL of water. The organic solution was concentrate to residue and the residue was diluted with 920 mL of Methanol. A solution of BPA 37 gr (0.515 eq) in 920 mL of Methanol was added. At the end of addition the mixture was stirred for 1 hour at 30° C. the obtained suspension was filtered and the solid was washed with 115 mL of Methanol.

58.1 gr of E-Clomiphene BPA salt were obtained.

HPLC Analysis (A/A%): 99.44% E-Chlomiphene, 0.00% Z-Clomiphene.

Example 4c

Purification of the Trans-Clomiphene Salt With Racemic Binaphthyl-Phosphoric Acid of Formula (VI)

In a round bottom flask was charged 76 gr of E-Clomiphene BPA salt (HPLC A/A%: 98.82% E-Clomiphene, 0.80% Z-Clomiphene), 500 mL of Toluene and 50 mL of water. The suspension was stirred at r.t. and then 20 mL of NaOH 30% were added. Then the obtained suspension was stirred for 2 hours then was filtered and the obtained solution was washed with 190 mL of water. The organic solution was concentrate to residual and the residue was diluted with 600 mL of Methanol. A solution of BPA 28 gr (0.515 eq) in 600 mL of Methanol was added. At the end of addition the mixture was stirred for 1.5h at 30° C. the obtained suspension was filtered and the solid was washed with 76 mL of Methanol.

53.9 gr of E-Clomiphene BPA salt were obtained.

HPLC Analysis (A/A%): 98.95% E-Chlomiphene, 0.10% Z-Clomiphene.

Example 5

Characterization of the Trans-Clomiphene Salt With Racemic Binaphthyl-Phosphoric Acid of Formula (VI)

Figure 4:
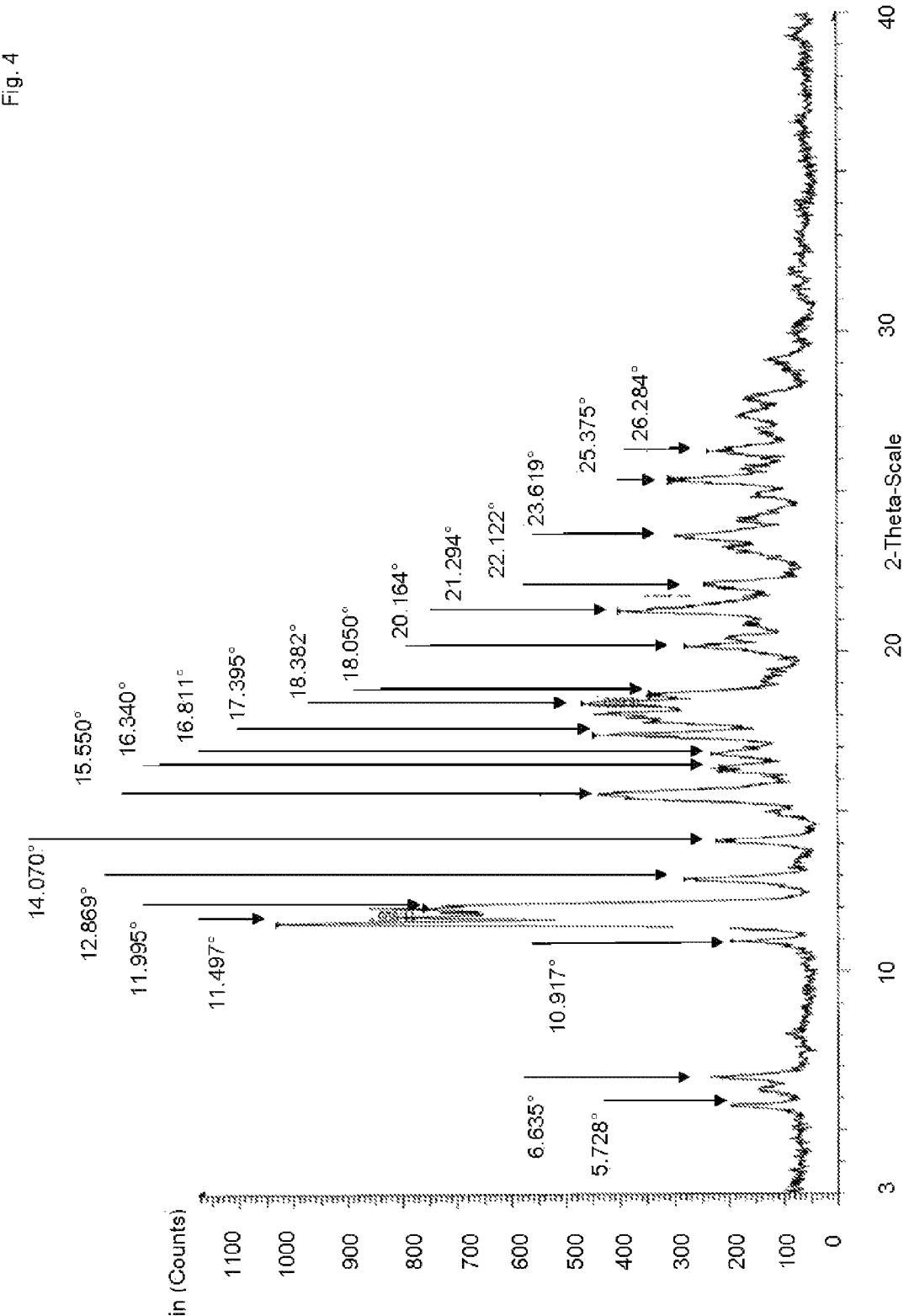
FIG. 4 shows the XPRD diffractogram of trans-Clomiphene salt with racemic binaphthyl-phosphoric acid of formula (VI).

XPRD diffractogram of the trans-Clomiphene salt with racemic binaphthyl-phosphoric acid of formula (VI) is shown in FIG. 4. Said crystal form is characterized by strong peaks at 2-theta values of 11.50 and 12.00.

The DSC analysis shows a melting point of 218.09° C. (onset) (see FIG. 5).

The trans configuration has been confirmed by 2D-H-NMR analysis.

Example 6a

Preparation of E-Clomiphene Citrate (1:1) From the Salt of Trans-Clomiphene With Racemic Binaphthyl-Phosphoric Acid of Formula (VI)

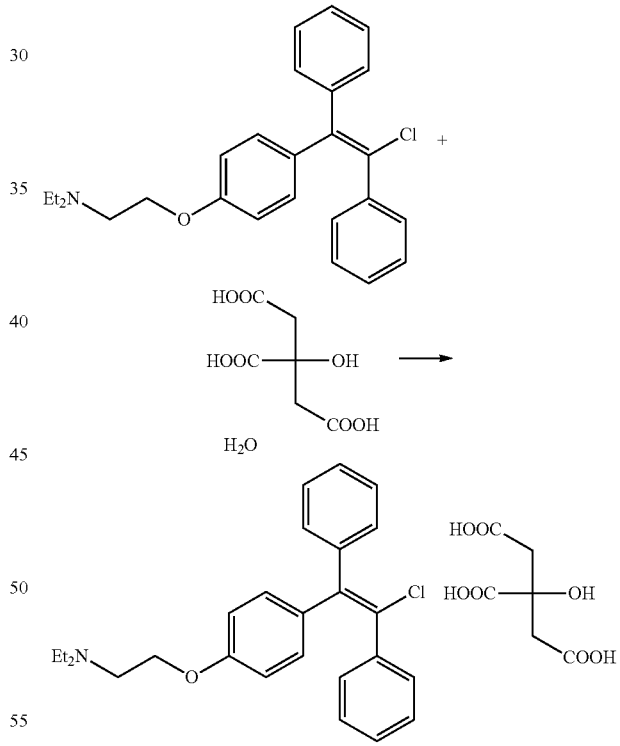

In a round bottom flask was charged 82 gr of E-Clomiphene BPA salt (HPLC A/A%: 99.40% E-Clomiphene, 0.34% Z-Clomiphene) and 500 mL of Toluene. The suspension was stirred at r.t. and then 20 mL of NaOH 30% and 50 mL of water were Methanol. Then the obtained suspension was stirred for 2 hours then was filtered and the obtained solution was washed with 200 mL of water. The organic solution was concentrate to residual and the residue was diluted with 105 mL of acetone. The solution was heated to 50° C. and a solution of citric acid monohydrate 27 gr in 166 mL of acetone was added. At the end of addition the mixture was stirred for 1 hour at 0° C. The obtained suspension was filtered and the solid was washed with 50 mL of acetone.

63.3 gr of E-Clomiphene Citrate salt (1:1) were obtained.

HPLC Analysis (A/A%): 99.75% E-Chlomiphene, 0.25% Z-Clomiphene.

Example 6b

Preparation of E-Clomiphene Citrate (1:1) From Trans-Clomiphene Salt With Racemic Binaphthyl-Phosphoric Acid of Formula (VI)

In a round bottom flask was charged 125 gr of E-Clomiphene BPA salt of formula (VI) and 1050 mL of Toluene. The suspension was stirred at r.t. and then 28 mL of NaOH 30% and 50 mL of water were added. Then the obtained suspension was stirred for 2 hours then was filtered and the obtained solution was washed with 250 mL of water. The organic solution was concentrate to residual and the residue was diluted with 310 mL of acetone. The solution was heated to 50° C. and a solution of citric acid monohydrate 41.5 gr in 500 mL of acetone was added. At the end of addition the mixture was stirred for 2 hours at 0° C. the obtained suspension was filtered and the solid was washed with 125 mL of acetone.

97.07 gr of E-Clomiphene Citrate salt were obtained.

HPLC Analysis (A/A%): 99.88% E-Chlomiphene, 0.05% Z-Clomiphene.

Example 6c

Preparation of E-Clomiphene Citrate (1:1) From the Salt of Trans-Clomiphene With Racemic Binaphthyl-Phosphoric Acid of Formula (VI)

In a round bottom flask was charged 109 gr of E-Clomiphene BPA salt of formula (VI), 950 mL of Toluene and 50 mL of water. The suspension was stirred at r.t. and then 29 mL of NaOH 30% were added. Then the obtained suspension was stirred for 2 hours then was filtered and the obtained solution was washed with 220 mL of water. The organic solution was concentrate to residual and the residue was diluted with 270 mL of acetone. The solution was heated to 50° C. and a solution of citric acid monohydrate 36 gr in 430 mL of acetone was added. At the end of addition the mixture was stirred for 2 hours at 0° C. The obtained suspension was filtered and the solid was washed with 110 mL of acetone.

82.7 gr of E-Clomiphene Citrate salt were obtained.

HPLC Analysis (A/A%): 99.90% E-Chlomiphene, 0.04% Z-Clomiphene.

K.F.=2.0%.

This solid product is characterized in Example 12.

Example 7

Synthesis of the Trans-Clomiphene Monocitrate From Trans-Clomiphene Base

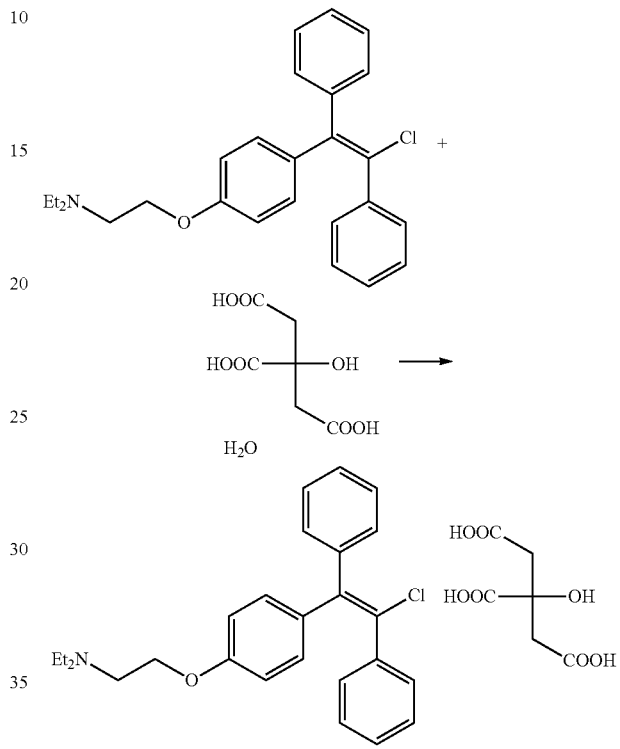

In a round bottom flask was charged 21.2 gr of E-Clomiphene free base (HPLC A/A%: 99.38% E-Clomiphene, 0.26% Z-Clomiphene) and 50 mL of acetone. The solution was heated to 50° C. and a solution of citric acid monohydrate 13.2 gr in 80 mL of acetone was added. At the end of addition the mixture was stirred for 4-5 h at 0° C. the obtained suspension was filtered and the solid was washed with 20 mL of acetone.

29.6 gr of E-Clomiphene monocitrate salt were obtained.

HPLC Analysis (A/A%): 99.62% E-Clomiphene, 0.38% Z-Clomiphene.

Example 8

Preparation and Characterization of the Salt of Anhydrous Trans-Clomiphene Monocitrate From Trans-Clomiphene Salt With Racemic Binaphthyl-Phosphoric Acid of Formula (VI)

In a round bottom flask was charged 155 gr of E-Clomiphene BPA salt of formula (VI), 1000 mL of Toluene and 150 mL of water. The suspension was stirred at r.t. and then 41 mL of NaOH 30% and 75 mL of MeOH were added. Then the obtained suspension was stirred then was filtered and the obtained solution was washed with 390 mL of water. The organic solution was concentrate to residual and the residue was diluted with 500 mL of acetone. The solution was heated to 50° C. and a solution of anhydrous citric acid 40 gr in 500 mL of acetone was added. At the end of addition the mixture was stirred for 2 hours at 0° C. the obtained suspension was filtered and the solid was wash with 155 mL of acetone. The solid was dried on vacuum at T =60° C. for 12 hours.

104.8 gr of E-Clomiphene Citrate salt were obtained.

HPLC Analysis (A/A%): 99.86% E-Clomiphene, 0.07% Z-Clomiphene.

K.F.=0.9%.

Example 9

Synthesis of the Compound Des-Ethyl Clomiphene Oxalate From Clomiphene Citrate as Mixture of Cis and Trans Isomers

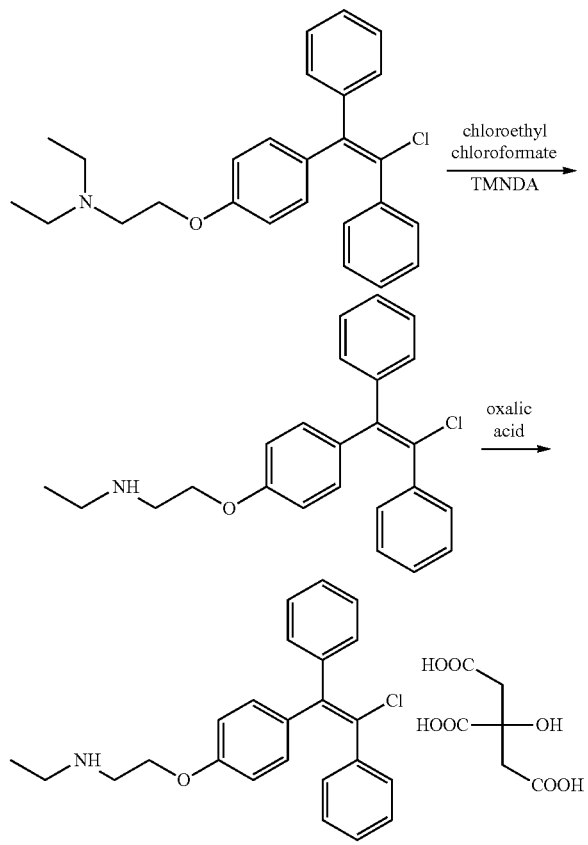

Step 1

A round bottomed flask with standard equipment was loaded with 14.7 g of clomiphene citrate, 50 mL of chlorobenzene and 50 mL of water. Into the flask, 8 mL of aqueous sodium hydroxide 30% w/w were dropped, up to pH 12. The reaction mixture was stirred, the layers were separated, the organic phase was washed with 3 x 20 mL of water and treated with sodium sulfate, obtaining a clear solution of Clomiphene in chlorobenzene.

Step 2

The clear solution of the previous step was treated with 8 g of tetramethylnaphtalendiamine and 5 mL of chloroethyl-chloroformate, then warmed to 80° C. The conversion was followed by HPLC. When the residual clomiphene was below 1%, the reaction mixture was cooled, treated slowly with 40 mL of methanol and heated to reflux for 2 hours. The methanol was then distilled off and the reaction mixture was treated with 20 mL of chlorobenzene, 30 mL of water and 8 mL of aqueous sodium hydroxide 30% w/w, up to pH 12. The layers were separated and the organic phase was dried with sodium sulfate and concentrated under vacuum to a residue, approx. 17 g. The crude product was purified by column chromatography using silica gel and eluent composed of 50 isopropyl acetate, 40 heptane, 5 dimethylethylamine. The order of elution is: Rf 0.9 tetramethylnaphthalendiamine; Rf 0.8 clomiphene; Rf 0.2 product.

The pure fractions were concentrated, obtaining 4.9 g of des-ethyl clomiphene as an oil.

Step 3

A round bottomed flask with standard equipment was loaded with 4.6 g of oil obtained in the previous step, with the addition of 13.8 mL of acetone and 0.46 g of decolorizing charcoal. After filtration, the clear solution was slowly dropped into another solution composed of 1.1 g of oxalic acid dissolved in 50.6 mL of acetone. The mixture was stirred 2 hours, filtered washing with 9.2 mL of acetone, the crude product taken up with 50.6 mL of acetone, stirred, filtered washing with 9.2 mL of acetone and dried at 50° C. under vacuum. The yield was 4.9 g of des-ethyl clomiphene oxalate.

Example 10

Analytical Method to Identify and Quantify the Impurity Des-Etil Clomiphene Into Chlomiphene or Enclomiphene Chromatographic conditions:
Column: Vydac 214TP C-4 250 mm/4.6 mm/5 µm
Temp. Column: 35° C.
Mobile Phase A: TFA 0.1% in water
Mobile Phase B: TFA 0.03% in ACN

| Time (min) | % A | % B |
|---|---|---|
| 0 | 80 | 20 |
| 24 | 40 | 60 |
| 30 | 10 | 90 |
| 31 | 80 | 20 |

Gradient:
Post run: 10 min.
Flow: 1.0 mL/min
Detector UV a 233 nm, bw 4 bn and 290 nm, bw 4 nm
Injection Volume: 5 µL (with needle-wash in ACN)
Run Time: 31 min
Sample diluent: H20/ACN (1:1)
Applying the conditions described above the expected retention times are as indicated below:

| Compound | RRT |
|---|---|
| Des-etil-Clomiphene - Isomer 1 | 0.93 |
| Des-etil-Clomiphene - Isomer 2 | 0.94 |
| Clomiphene or Enclomiphene | 1.00 |

Example 11

Analytical Method to Identify and Quantify Cis-Clomiphene and Trans-Clomiphene and to Determine the Purity and Ratio Thereof Chromatographic conditions:
Dim. Column: 250 mm×4.6 mm, 5 μm
Stationaly phase: Butyl sylane (USP phase L26, Vydac 4C is suggested)
Temp. Column: room temperature
Mobile Phase: Methanol/water/triethylamine 55:45:0.3 v/v
Adjust at pH 2.5 with phosphoric acid
Flow: 1.0 mL/min
Detector UV a 233 nm,
Injection Volume: 10 μL
Sample diluent: mobile phase.
Applying the conditions described above the expected retention times are as indicated below:

| Compound | RRT |
|---|---|
| cis-Clomiphene | 1.00 |
| Trans-Clomiphene | 1.09 |

Example 12

Characterization of the Solid Form of Trans-Clomiphene Monocitrate Prepared According to Example 6c XPRD Analysis XRPD analysis was performed using a PANalytical X'Pert diffractometer with Cu Ka radiation in Bragg-Brentano geometry. The system is equipped with a monodimensional, real time multiple strip detector. The diffractogram was recorded from 3° to 40° (2θ) at a scan rate of 17.6° per minute (see FIG. 5).

The solid form of trans-Clomiphene monocitrate exhibits a characteristic X-ray powder diffraction pattern with characteristic peaks expressed in 2-Theta values (2θ): 5.69 (s), 9.64 (s), 10.86 (m), 11.45 (s), 12.64 (vs), 14.75 (m), 16.35 (m), 17.02 (m), 18.69 (m), 20.51 (m), 21.68 (m), 23.58 (m), 24.82 (m), 31.2 (w); wherein (vs)=very strong intensity; (m)=medium intensity; (w)=weak intensity.

The solid form of trans-Clomiphene monocitrate exhibits a characteristic X-ray powder diffraction pattern with characteristic stronger peaks expressed in 2-Theta values (2θ): 5.69 (s), 9.64 (s), 11.45 (s), 12.64 (vs).

Crystal Habit

The solid form of trans-Clomiphene monocitrate has non-needle-shaped crystal.

Karl Fischer

Karl Fischer analyses were recorded with a Metrohm 787 KF Trinito. The product was dissolved in MeOH. Two samples were analyzed using the following reactants: Hydranal-Composite 5 (Riedel de Haen Ref. 34805), Hydranal Methanol Rapid (Riedel de Haen Ref. 37817) and Hydranal Water Standard 1.0 (Riedel de Haen Ref. 34828 used to calculate the factor).

K.F. =2.0%.

DSC

DSC analysis was recorded with a Mettler DSC822e. A sample of 3.5000 mg was weighed into a 40 μL aluminium crucible with a pinhole lid and was heated, under nitrogen (50 mL/min), at 10 ° C./min from 30 to 300 ° C.

The new solid form of Trans-Clomiphene citrate is characterized by an endothermic sharp peak corresponding to the melting point with an onset at 146.83° C. (fusion enthalpy −54.56 J/g), measured by DSC analysis (10 ° C./min). At 169.4° C. (onset) begin a broad endothermic peak.

Thus, trans-Clomiphene monocitrate shows a melting point of about 147° C. measuted by DSC.

TGA

Thermogravimetric analysis was recorded in a thermogravimetric analyzer Mettler TGA/SDTA851e. A sample of 16.9805 mg was weighed into a 70 μL alumina crucible with a pinhole lid and was heated at 10° C./min from 30 to 280 ° C., under nitrogen (50 mL/min).

The TG analysis of trans-Clomiphene monocitrate shows a 1.58% weight loss before the melting point well before the melting point and the boiling point of the water. This loss of weight could come from the elimination of acetone traces.

The invention claimed is:

1. A process for the preparation of Clomiphene and salts thereof, comprising reacting a mixture of geometric isomers of formula (V-E) and (V-Z) or salts thereof:

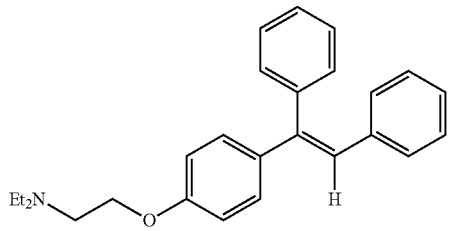

(V-E)

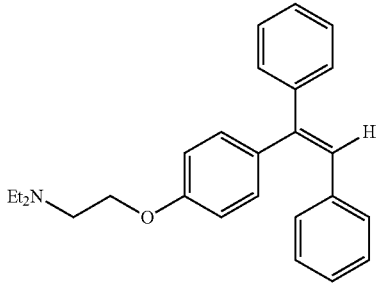

(V-Z)

in an organic solvent with a chlorinating agent, wherein the reacting is performed in presence of acetic acid or trifluoroacetic acid.

2. The process according to the claim 1, wherein the amount of acetic acid or trifluoroacetic acid is between 1 and 3 volumes.

3. The process according to claim 1, wherein the organic solvent is methylene chloride.

4. The process according to claim 2, wherein the amount of methylene chloride is between 5 and 11 volumes.

5. The process according to claim 1, wherein the amount of acetic acid or trifluoroacetic acid is between 1 and 3 volumes and the amount of methylene chloride is between 5 and 11 volumes.

6. The process according to the claim 5, wherein the amount of acetic acid or trifluoroacetic acid is about 2 volumes and the amount of methylene chloride is about 8 volumes.

7. The process according to claim 1, wherein the reacting is performed at a temperature between 20° C. and 40° C.

8. The process according to claim 1, wherein the amount of chlorinating agent is in the range of from 0.45 to 0.60 molecular equivalents.

9. The process according to claim 1, wherein the chlorinating agent is dichlorodimethylhydantoin.

10. The process according to claim 1, wherein the reacting is carried out under anhydrous conditions.

11. A process for the preparation of trans-Clomiphene and salts thereof, comprising reacting a mixture of geometric isomers of formula (V-E) and (V-Z) or salts thereof:

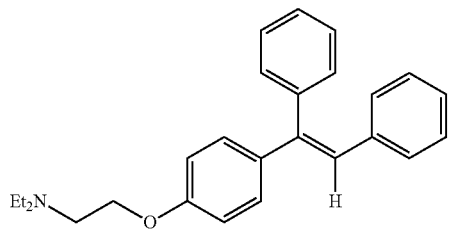
(V-E)

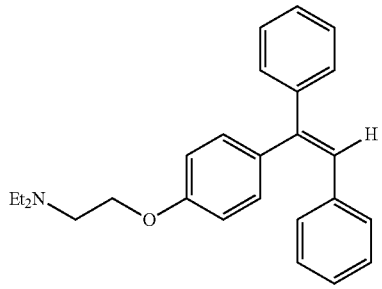
(V-Z)

in an organic solvent with a chlorinating agent, wherein the organic solvent is methylene chloride and the reacting is performed in presence of acetic acid or trifluoroacetic acid.

12. The process according to claim 1, wherein the Clomiphene prepared by said process is a mixture of trans-Clomiphene and cis-Clomiphene in ratio from 75:25 to 99:1.

* * * * *